(12) United States Patent
Zheng et al.

(10) Patent No.: US 10,571,393 B2
(45) Date of Patent: Feb. 25, 2020

(54) TERAHERTZ GAS DETECTION METHOD AND DEVICE BASED ON GREGORY DOUBLE REFLECTION ANTENNA

(71) Applicant: Tsinghua University, Beijing (CN)

(72) Inventors: Xiao-Ping Zheng, Beijing (CN); Xiao-Jiao Deng, Beijing (CN); Hua Geng, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 16/445,219

(22) Filed: Jun. 19, 2019

(65) Prior Publication Data
US 2019/0317017 A1 Oct. 17, 2019

Related U.S. Application Data

(63) Continuation of application No. PCT/CN2018/092444, filed on Jun. 22, 2018.

(30) Foreign Application Priority Data

Apr. 13, 2018 (CN) .......................... 2018 1 0332530

(51) Int. Cl.
*G01N 21/3581* (2014.01)
*G01J 3/42* (2006.01)

(52) U.S. Cl.
CPC ............ *G01N 21/3581* (2013.01); *G01J 3/42* (2013.01)

(58) Field of Classification Search
CPC .............................. G01N 21/3581; G01J 3/42
(Continued)

(56) References Cited

U.S. PATENT DOCUMENTS 3,548,342 A * 12/1970 Maxey .................... H03M 1/82
332/106
6,479,822 B1 * 11/2002 Nelson ............... G01N 21/3581
250/338.1
(Continued)

FOREIGN PATENT DOCUMENTS

CN 202196176 4/2012
CN 102759753 10/2012
(Continued)

OTHER PUBLICATIONS

Shimizu, N. et al, "8-2 Stand-off Gas Sensing System Based on Terahertz Spectroscopy", Journal of the National Institute of Information and Communication Technology, 55(1), 165-170 (Year: 2008).*
(Continued)

*Primary Examiner* — David P Porta
*Assistant Examiner* — Blake C Riddick

(57) ABSTRACT

The present disclosure relates to a terahertz-based high-risk chemical detecting device, which includes a terahertz wave generating unit, a terahertz wave transmitting and receiving unit and an echo analysis unit. The terahertz wave generating unit is configured for generating a terahertz detection signal, a terahertz reference signal and a terahertz local oscillation signal. The terahertz wave transceiver unit is configured to transmit the terahertz detection signal and the terahertz reference signal to a high-risk chemical to be tested, and receive information about carrying a high-risk chemical to be tested. The terahertz echo signal is configured to analyze the terahertz echo signal and the terahertz local oscillation signal to obtain information about a high-risk chemical to be tested. The present disclosure also relates to a terahertz-based high-risk chemical detecting method.

11 Claims, 2 Drawing Sheets

(58) Field of Classification Search
USPC ..... 250/336.1, 338.1, 338.4, 339.01, 339.06, 250/339.07
See application file for complete search history.

(56) References Cited

U.S. PATENT DOCUMENTS

| | | | | |
|---|---|---|---|---|
| 6,556,306 | B2* | 4/2003 | Jiang | G01N 21/41 356/487 |
| 7,550,734 | B1* | 6/2009 | Lee | B82Y 20/00 250/370.12 |
| 7,876,423 | B1* | 1/2011 | Roth | G01B 11/0625 356/27 |
| 8,035,083 | B1 | 10/2011 | Kozlov et al. | |
| 8,358,420 | B1 | 1/2013 | DeWitt et al. | |
| 8,748,822 | B1* | 6/2014 | Gerecht | G01J 3/42 250/339.07 |
| 8,786,508 | B1* | 7/2014 | Edwards | H01Q 15/14 343/781 P |
| 9,400,214 | B1* | 7/2016 | Demers | G01J 3/0256 |
| 2002/0067480 | A1* | 6/2002 | Takahashi | G01N 21/3581 356/317 |
| 2007/0138392 | A1* | 6/2007 | Cole | G01N 21/49 250/341.1 |
| 2008/0149819 | A1* | 6/2008 | Zhdaneev | G01N 21/3581 250/255 |
| 2008/0179528 | A1* | 7/2008 | Demers | G01J 3/42 250/341.1 |
| 2009/0056455 | A1* | 3/2009 | Ouchi | G01N 21/3581 73/643 |
| 2009/0283680 | A1* | 11/2009 | Logan, Jr. | G01J 3/10 250/339.07 |
| 2010/0148069 | A1* | 6/2010 | Ouchi | G01N 21/4795 250/341.8 |
| 2010/0277726 | A1* | 11/2010 | Logan, Jr. | G01J 3/10 356/326 |
| 2011/0079720 | A1* | 4/2011 | Heidari | G01J 3/28 250/340 |
| 2011/0127432 | A1 | 6/2011 | Federici et al. | |
| 2011/0198501 | A1* | 8/2011 | Ouchi | A61B 5/0059 250/343 |
| 2011/0267599 | A1* | 11/2011 | Hurley | G01J 3/02 356/51 |
| 2012/0191371 | A1* | 7/2012 | Arbab | G01N 21/3586 702/28 |
| 2012/0223229 | A1* | 9/2012 | Itsuji | G01J 3/0205 250/330 |
| 2012/0326039 | A1* | 12/2012 | Demers | G01J 3/10 250/338.4 |
| 2013/0048859 | A1* | 2/2013 | Scheller | G01N 21/3586 250/339.08 |
| 2013/0222571 | A1* | 8/2013 | Kychakoff | G01J 11/00 348/82 |
| 2013/0265573 | A1* | 10/2013 | Pate | G01J 3/443 356/311 |
| 2013/0328697 | A1* | 12/2013 | Lundy | G08C 17/02 340/870.16 |
| 2015/0234047 | A1* | 8/2015 | Fukasawa | G01N 21/3581 250/341.8 |
| 2018/0325366 | A1* | 11/2018 | Xie | A61B 1/018 |
| 2019/0041200 | A1* | 2/2019 | Saeedkia | G01B 11/0625 |
| 2019/0131704 | A1* | 5/2019 | Urzhumov | H01Q 15/14 |
| 2019/0150719 | A1* | 5/2019 | Jarrahi | H01L 27/14601 |
| 2019/0198999 | A1* | 6/2019 | Ashrafi | H04L 5/06 |

FOREIGN PATENT DOCUMENTS

| | | |
|---|---|---|
| CN | 103148940 | 6/2013 |
| CN | 103954584 | 7/2014 |
| CN | 104034690 | 9/2014 |
| CN | 104038706 | 9/2014 |
| CN | 104865221 | 8/2015 |
| CN | 204855366 | 12/2015 |
| CN | 105572667 | 5/2016 |
| CN | 105866850 | 8/2016 |
| CN | 105891900 | 8/2016 |
| CN | 106596461 | 4/2017 |
| CN | 106896081 | 6/2017 |
| CN | 107064049 | 8/2017 |
| CN | 107340269 | 11/2017 |

OTHER PUBLICATIONS 0.3 THz Compact Reflector Antenna. pp. 52-54, 1 issue, vol. 36, «Modern Radar».

Reflectarray Antenna at Terahertz Using Graphene. pp. 253-256, vol. 12, «IEEE Antennas and Wireless Propagation Letters».

* cited by examiner

TERAHERTZ GAS DETECTION METHOD AND DEVICE BASED ON GREGORY DOUBLE REFLECTION ANTENNA

CROSS-REFERENCE TO RELATED APPLICATIONS

This application claims all benefits accruing under 35 U.S.C. § 119 from China Patent Application No. 201810332530.4, filed on Apr. 13, 2018 in the State Intellectual Property Office of China, the content of which is hereby incorporated by reference. This application is a continuation under 35 U.S.C. § 120 of international patent application PCT/CN2018/092444 filed on Jun. 22, 2018, the content of which is also hereby incorporated by reference.

FIELD

The present application relates to the environmental safety field, and particularly to terahertz based methods and devices for detecting a high-risk chemical.

BACKGROUND

Aerosol clouds can be formed and rapidly spread after release or leakage of a high-risk chemical such as chemical weapons, causing widespread and fatal damage to human and environment. Fast and accurate the high-risk chemical detecting and early warning can provide important information for subsequent operations such as protection, destruction, decontamination, and evacuation, and so can greatly reduce the damages.

At present, methods for detecting the high-risk chemical are gas chromatography -mass spectrometry (GC-MS), ion migration, nuclear magnetic resonance (NMR) spectroscopy, ultraviolet laser-induced fluorescence detection, and surface-enhanced Raman scattering spectroscopy. Among them, the GC-MS, ion migration, NMR spectroscopy, and ultraviolet laser-induced fluorescence detection require sampling or pretreatment, and therefore are not suitable for on-site detection, while surface-enhanced Raman scattering spectrometry is not suitable for remote detection.

SUMMARY

What is needed, therefore, is to provide terahertz technology based methods and devices for detecting a high-risk chemical to achieve on-site detection of the high-risk chemical.

A device for detecting a high-risk chemical based on terahertz technology comprising:
  a terahertz wave generating unit, configured to generate a terahertz detection signal, a terahertz reference signal, and a terahertz local oscillation signal, to transmit the terahertz detection signal and the terahertz reference signal to the terahertz wave transceiver unit, and to transmit the terahertz local oscillation signal to the echo analysis unit;
  a terahertz wave transceiver unit, configured to transmit the terahertz detection signal and the terahertz reference signal to the high-risk chemical to be tested, and to receive a terahertz echo signal carrying information of the high-risk chemical to be tested; and
  an echo analysis unit, configured to modulate and analyze the terahertz local oscillation signal and the terahertz echo signal to obtain information of the high-risk chemical to be tested.

In one embodiment, the terahertz wave generating unit comprises a digital signal generating module and a digital to pulse conversion module.

The digital signal generating module is configured to generate a digital signal and send the digital signal to the digital to pulse conversion module.

The digital to pulse conversion module is configured to convert the digital signal to the terahertz detection signal, the terahertz reference signal, and the terahertz local oscillation signal.

In one embodiment, the terahertz wave transceiver unit comprises a transceiver switch and a dual-offset Gregorian reflector antenna.

The transceiver switch is configured to control the dual-offset Gregorian reflector antenna to transmit the terahertz detection signal and the terahertz reference signal, and to control the dual-offset Gregorian reflector antenna to receive the terahertz echo signal.

In one embodiment, the controlling of the dual-offset Gregorian reflector antenna by the transceiver switch to transmit the terahertz detection signal and the controlling of the dual-offset Gregorian reflector antenna by the transceiver switch to receive the terahertz echo signal are performed separately.

In one embodiment, the dual-offset Gregorian reflector antenna comprises a primary reflecting surface, a secondary reflecting surface, and a feed.

In one embodiment, the echo analysis unit comprises a detector and a signal processor, wherein
  the detector receives the terahertz local oscillation signal and the terahertz echo signal, and modulates the terahertz local oscillation signal and the terahertz echo signal to obtain a detection result; and
  the signal processor receives the detection result and analyzes the detection result to obtain the type and concentration of the high-risk chemical to be tested.

In one embodiment, the detector comprises a Schottky diode mixer.

In one embodiment, the detection result comprises a terahertz absorption spectrum of the high-risk chemical to be tested or a parameter of the terahertz echo signal.

In one embodiment, the device further comprises a reflecting unit configured to reflect the terahertz echo signal back to the dual-offset Gregorian reflector antenna.

A method for detecting a high-risk chemical based on terahertz waves comprising:
  receiving a digital signal, converting the digital signal to a terahertz detection signal, a terahertz reference signal, and a terahertz local oscillation signal;
  transmitting the terahertz detection signal to the high-risk chemical to be tested, and obtaining a terahertz echo signal;
  modulating and analyzing the terahertz echo signal and the terahertz local oscillation signal to obtain information of a terahertz absorption spectrum; and
  analyzing the information of the terahertz absorption spectrum to obtain the type and the concentration information of the high-risk chemical.

Details of one or more embodiments of the present disclosure are set forth in the accompanying drawings and description below. Other features, purposes, and advantages of the disclosure will be apparent from the description and appended claims.

BRIEF DESCRIPTION OF THE DRAWINGS

Implementations are described by way of example only with reference to the attached figures.

DETAILED DESCRIPTION

Numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described.

The present disclosure provides embodiments of terahertz based methods and devices for detecting a high-risk chemical, through whose terahertz wave transceiver unit to transmit and receive terahertz waves in a relatively long distance, and through the analyzing of the terahertz echo signal to obtain information of information of the high-risk chemical, realizes a long-distance on-site detection of the high-risk chemical to quickly, accurately and safely monitoring and warning of the high-risk chemical.

Figure 1:
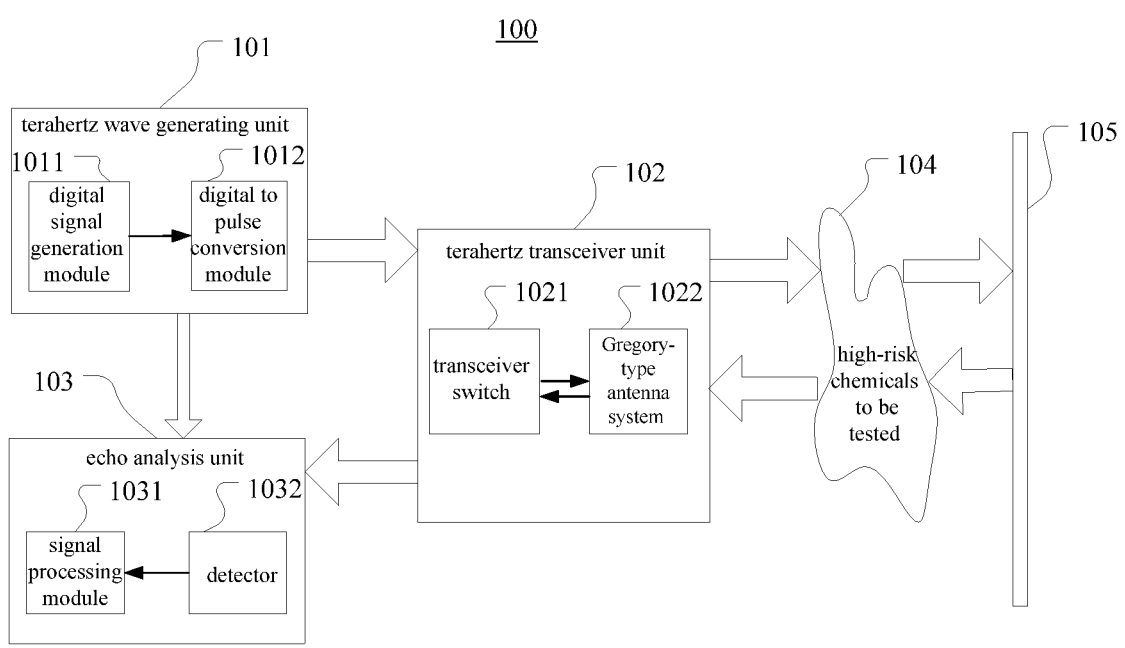
FIG. 1 is a schematic view of one embodiment of devices for detecting a high-risk chemical based on terahertz waves.

Referring to FIG. 1, an embodiment of a terahertz based device 100 for detecting a high-risk chemical comprises a terahertz wave generating unit 101, a terahertz wave transceiver unit 102, and an echo analysis unit 103.

In one embodiment, the terahertz wave generating unit 101 is configured to generate a terahertz detection signal, a terahertz reference signal, and a terahertz local oscillation signal, configured to transmit the terahertz detection signal and the terahertz reference signal to the terahertz wave transceiver unit 102, and configured to transmit the terahertz local oscillation signal to the echo analysis unit 103.

In one embodiment, the terahertz wave generating unit 101 includes a digital signal generation module 1011 and a digital to pulse conversion module 1012. Specifically, the digital signal generating module 1011 is configured to generate a digital signal and send the digital signal to the digital to pulse conversion module 1012. The digital to pulse conversion module 1012 is configured to convert the digital signal to the terahertz detection signal, the terahertz reference signal, and terahertz local oscillation signal. The generation of terahertz waves by the digital to pulse conversion module 1012 can effectively reduce the number of components, thereby achieving a miniaturization of the terahertz detection device. In another embodiment, the terahertz wave generating unit 101 can be a laser module.

In one embodiment, the terahertz wave transceiver unit 102 is configured to transmit the terahertz detection signal and the terahertz reference signal to the high-risk chemical to be tested 104, and to receive the terahertz echo signal carrying the information of the high-risk chemical to be tested 104. The terahertz echo signal refers to the signal reflected by the reflecting unit 105 after the terahertz detection signal and the terahertz reference signal are sent to the high-risk chemical to be tested 104. In an embodiment, a distance from the terahertz transceiver unit 102 to the high-risk chemical to be tested 104 is within 100 meters. It can be understood that the distance between the terahertz transceiver unit 102 and the high-risk chemical to be tested 104 is not limited to 100 meters. The terahertz transmitting power can be adjusted according to the distance and weather condition, thereby enabling the detection of the high-risk chemical at different distances to the terahertz transceiver unit 102.

In one embodiment, the terahertz wave transceiver unit 102 includes a transceiver switch 1021 and a dual-offset Gregorian reflector antenna 1022. The transceiver switch 1021 is configured to control the Gregorian reflector antenna 1022 to transmit the terahertz detection signal and the terahertz reference signal. The transceiver switch 1021 is also configured to control the dual-offset Gregorian reflector antenna to receive the terahertz echo signal. In an embodiment, the dual-offset Gregorian reflector antenna 1022 includes a primary reflecting surface, a secondary reflecting surface, and a feed. As an optional embodiment, the controlling of the dual-offset Gregorian reflector antenna 1022 by the transceiver switch 1021 to transmit the terahertz detection signal and the controlling of the dual-offset Gregorian reflector antenna 1022 by the transceiver switch 1021 to receive the terahertz echo signal are performed separately. As an alternative embodiment, the dual-offset Gregorian reflector antenna 1022 simultaneously implements both receiving and transmitting functions. Specifically, the dual-offset Gregorian reflector antenna 1022 has two focal points, and the two focal points are located on the two reflecting surfaces, so the dual-offset Gregorian reflector antenna 1022 can have two feeds, thereby enabling simultaneous implement of the receiving and transmitting. In an embodiment, in the dual-offset Gregorian reflector antenna 1022, the spacing between the feed and the secondary reflecting surface is increased to achieve a far-field condition.

In an embodiment, the echo analysis unit 103 is configured to modulating analyze the terahertz echo signal and the terahertz local oscillation signal to obtain information of the high-risk chemical to be tested. Specifically, the terahertz detection signal and the terahertz reference signal are sent to detect the high-risk chemical, and the terahertz echo signal is obtained. The terahertz echo signal is reflected by the reflecting unit 105 to the terahertz transceiver unit 102, and the terahertz transceiver unit 102 transmits the terahertz echo signal to the echo analysis unit 103. In an embodiment, the echo analysis unit 103 includes a detector 1032 and a signal processing module 1031. In one embodiment, the detector 1032 can include a detector array or a single detector. The detector array can increase the speed and range of detection. In an embodiment, the detector 1032 comprises a Schottky diode mixer or other element, which can detect in room temperature.

In an embodiment, the detection result of the terahertz echo signal by the detector 1032 includes obtaining a thickness L of the high-risk chemical to be tested, a echo power $Pr(\lambda)$ of the terahertz echo signal, a transmission power of the terahertz detection signal $Pt(\lambda)$, a target absorption coefficient $\alpha(\lambda)$, a wavelength of the terahertz detection signal $\lambda_0$, and a wavelength of the terahertz reference signal $\lambda_\omega$.

In an embodiment, the signal processing module 1031 receives the detection result, and analyzes the detection result to obtain the type and the concentration of the high-risk chemical to be tested. In one of the embodiments, the signal processing module 1031 compares the frequency of the absorption peak in the terahertz absorption spectrum with frequencies of absorption peaks of known substances in database to obtain the type of the high-risk chemical to be tested. As an alternative embodiment, the signal processing module 1031 can obtain relative concentrations of the high-risk chemical according to Lambert-beer's law, by determining a size of the absorption peak in terahertz absorption spectrum, and comparing to a reference standard sample. As an alternative embodiment, according to Lambert-beer's law, the signal processing module 1031 obtains the concentration of the high-risk chemical by the following formula:

$$C = \frac{1}{2[\propto(\lambda_0) - \propto(\lambda_\omega)]L} \ln\left(\frac{P_r(\lambda_0)P_t(\lambda_\omega)}{P_r(\lambda_\omega)P_t(\lambda_0)}\right)$$

In an embodiment, the device 100 further includes a reflective unit 105 configured to reflect the terahertz echo signal back to the terahertz wave transceiver unit. As an alternative embodiment, the reflective unit 105 is a mirror. It can be understood that the reflecting unit 105 is not limited to a mirror, but can be other devices capable of reflecting the terahertz echo signal back to the terahertz transceiver unit 102, such as a smooth surface of a wall.

Figure 2:
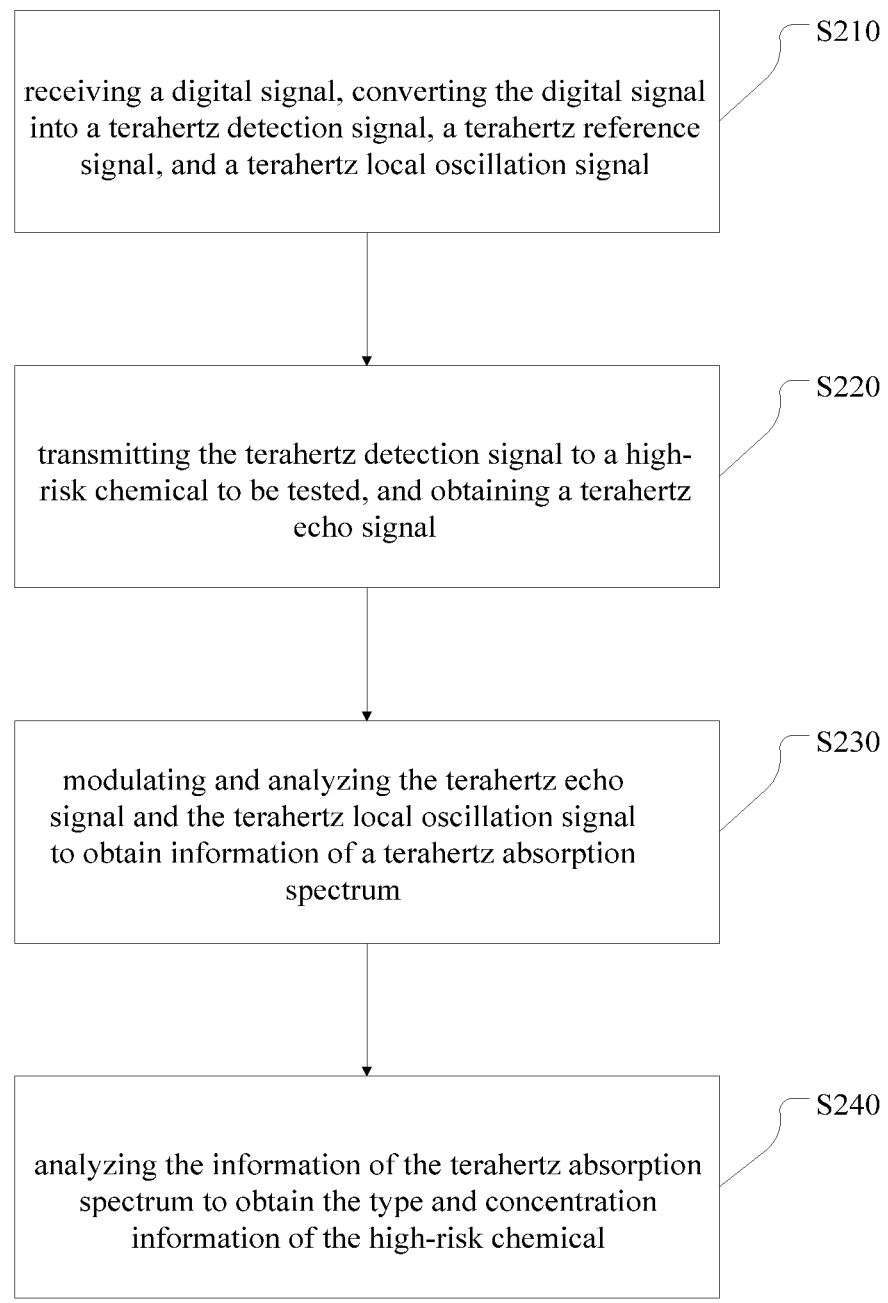
FIG. 2 shows a flowchart of one embodiment of a method for detecting a high-risk chemical based on terahertz waves.

Referring to FIG. 2, one embodiment of a method for detecting a high-risk chemical based on terahertz waves comprising:
- S210, receiving a digital signal, converting the digital signal into a terahertz detection signal, a terahertz reference signal, and a terahertz local oscillation signal;
- S220, transmitting the terahertz detection signal to the high-risk chemical to be tested, and obtaining a terahertz echo signal;
- S230, modulating and analyzing the terahertz echo signal and the terahertz local oscillation signal to obtain information of a terahertz absorption spectrum; and
- S240, analyzing the information of the terahertz absorption spectrum to obtain the type and the concentration information of the high-risk chemical.

FIG. 2 illustrates a schematic flow chart of the method. It should be understood that although the steps in the flowchart of FIG. 2 are sequentially shown as indicated by the arrows, these steps are not necessarily performed in the order indicated by the arrows. Except as explicitly stated herein, the execution of these steps is not strictly limited, and may be performed in other sequences. Moreover, at least some of the steps in FIG. 2 may include multiple sub-steps or multiple stages, which are not necessarily performed at the same time, but may be executed at different times, and the order of execution thereof is not necessarily sequential. The steps may be performed alternately or alternately with at least a portion of other steps, sub-steps, or stages of other steps.

For some atmospheric high-risk chemical having macromolecules, spectral lines obtained using terahertz waves result in sharper absorption peaks and less linear overlap, which makes the identification of the high-risk chemical in the atmosphere easier.

The terahertz waves have good penetrability in many dielectric materials and non-polar liquids compared to other detection means, so terahertz waves can be used for see-through imaging of opaque objects. In addition, since the typical wavelength of terahertz waves is much larger than the size of soot particles in the air, these suspended soot particles scatter the terahertz waves much less than the scattering of other electromagnetic waves, so the terahertz waves can be used in a more complex on-site environment.

The terahertz waves have absorption peaks and reflection peaks at different frequencies for different substances which results fingerprint spectrums of the substances, thus the terahertz waves can efficiently and accurately calibrate the species of the high-risk chemical in the atmosphere by comparing with the existing fingerprint information of the high-risk chemical in database. The concentration of the high-risk chemical in the atmosphere can be determined according to the amplitudes or areas of the absorption peaks or the reflection peaks, or other features of the absorption peaks or the reflection peaks that vary with the concentration of the high-risk chemical in the atmosphere.

Terahertz waves are submillimeter waves, and the photon energy and characteristic temperature of the terahertz waves are very low. Energy of a photon having a frequency of 1 THz (corresponding to 33 cm$^{-1}$) is 4.1 MeV, and the characteristic temperature thereof is 48K, which is lower than the bond energy of various chemical bonds. The photon energy required for ionizing biological tissues usually reaches 16 eV. The energy of the terahertz waves is far from ionizing biological tissues or cells, so the terahertz waves may not cause harmful ionization reactions.

In the above-mentioned terahertz wave based device and method for detecting the high-risk chemical, the generated terahertz pulse is transmitted and received by the terahertz transceiver unit over a long distance. Through analyzing of the terahertz echo signal to obtain information of information of the high-risk chemical, a long-distance on-site detection of the high-risk chemical can be realized to quickly, accurately and safely monitoring and warning of the high-risk chemical.

Finally, it should also be noted that here relational terms such as first and second are used merely to distinguish one entity or operation from another entity or operation, and do not necessarily require or imply these entities. There is any such actual relationship or order between operations. Furthermore, the term "comprises" or "includes" or any other variants thereof is intended to encompass a non-exclusive inclusion, such that a process, method, article, or device that comprises a plurality of elements includes not only those elements but also other elements, or elements that are inherent to such a process, method, item, or device. An element that is defined by the phrase "comprising a . . . " does not exclude the presence of additional equivalent elements in the process, method, item, or device that comprises the element.

The various embodiments in the present specification are described in a progressive manner, and each embodiment focuses on differences from other embodiments, and the same similar parts between the various embodiments may be referred to each other.

The above-mentioned description of the disclosed embodiments enables those skilled in the art to implement or use the present application. Various modifications to these embodiments are obvious to those skilled in the art, and the general principles defined herein may be implemented in other embodiments without departing from the spirit or scope of the application. Therefore, the present application is not limited to the embodiments shown herein, but the broadest scope consistent with the principles and novel features disclosed herein.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:
1. A device for detecting a chemical based on terahertz waves comprising:
   a terahertz wave generator, configured to generate a terahertz detection signal, a terahertz reference signal, and a terahertz local oscillation signal, to transmit the terahertz detection signal and the terahertz reference signal to a terahertz wave transceiver, and to transmit the terahertz local oscillation signal to an echo analyzer;

the terahertz wave transceiver, configured to transmit the terahertz detection signal and the terahertz reference signal to the chemical to be tested, and to receive a terahertz echo signal carrying information of the chemical to be tested, the terahertz wave transceiver comprising a transceiver switch and a dual-offset Gregorian reflector antenna, the transceiver switch being configured to control the dual-offset Gregorian reflector antenna to transmit the terahertz detection signal and the terahertz reference signal to the chemical, and to control the dual-offset Gregorian reflector antenna to receive the terahertz echo signal; and the echo analyzer, configured to modulate and analyze the terahertz local oscillation signal and the terahertz echo signal to obtain information of the chemical to be tested.

2. The device of claim 1, wherein the terahertz wave generator comprises a digital signal generator and a digital to pulse converter.

3. The device of claim 2, wherein the digital signal generator is configured to generate a digital signal and send the digital signal to the digital to pulse converter.

4. The device of claim 2, wherein the digital to pulse converter is configured to convert the digital signal to the terahertz detection signal, the terahertz reference signal, and the terahertz local oscillation signal.

5. The device of claim 1, wherein the controlling of the dual-offset Gregorian reflector antenna by the transceiver switch to transmit the terahertz detection signal and the controlling of the dual-offset Gregorian reflector antenna by the transceiver switch to receive the terahertz echo signal are performed separately.

6. The device of claim 1, wherein the dual-offset Gregorian reflector antenna comprises a primary reflecting surface, a secondary reflecting surface, and a feed.

7. The device of claim 1, wherein the echo analyzer comprises a detector and a signal processor, wherein the detector receives the terahertz local oscillation signal and the terahertz echo signal, and modulates the terahertz local oscillation signal and the terahertz echo signal to obtain a detection result; and the signal processor receives the detection result and analyzes the detection result to obtain the type and concentration of the chemical to be tested.

8. The device of claim 7, wherein the detector comprises a Schottky diode mixer.

9. The device of claim 7, wherein the detection result comprises a terahertz absorption spectrum of the chemical to be tested or a parameter of the terahertz echo signal.

10. The device of claim 1 further comprising a reflector configured to reflect the terahertz echo signal back to the dual-offset Gregorian reflector antenna.

11. A method for detecting a chemical based on terahertz waves comprising:

receiving a digital signal, converting the digital signal to a terahertz detection signal, a terahertz reference signal, and a terahertz local oscillation signal;

transmitting the terahertz detection signal by a dual-offset Gregorian reflector antenna to the chemical to be tested, and obtaining a terahertz echo signal by the dual-offset Gregorian reflector antenna;

modulating and analyzing the terahertz echo signal and the terahertz local oscillation signal to obtain information of a terahertz absorption spectrum; and analyzing the information of the terahertz absorption spectrum to obtain type and concentration information of the chemical.

* * * * *